United States Patent [19]

Freenor, III

[11] 4,456,467
[45] Jun. 26, 1984

[54] 1-METHYLENE CARBONYL DERIVATIVES OF 3-ARYLOXY-4-PHENYL-AZET-2-ONE

[75] Inventor: Francis J. Freenor, III, Richmond, Calif.

[73] Assignee: Chevron Research Company, San Francisco, Calif.

[21] Appl. No.: 225,886

[22] Filed: Jan. 19, 1981

Related U.S. Application Data

[63] Continuation of Ser. No. 120,428, Feb. 11, 1980, abandoned.

[51] Int. Cl.³ .................. C07D 205/08; A01N 43/44
[52] U.S. Cl. .................................. 71/88; 71/76; 260/239 A; 564/396
[58] Field of Search ............... 260/239 AL; 71/76, 88

[56] References Cited

U.S. PATENT DOCUMENTS 4,181,800 1/1980 Kamiya et al. ............... 544/180
4,207,234 6/1980 Kamiya et al. ............... 260/239 A Primary Examiner—Mark L. Berch
Attorney, Agent, or Firm—S. R. LaPaglia; T. G. DeJonghe; S. L. Biggs

[57] ABSTRACT

1-Methylene carbonyl derivatives of 3-aryloxy-4-phenyl-azet-2-ones are effective plant-growth regulators.

10 Claims, No Drawings

1-METHYLENE CARBONYL DERIVATIVES OF 3-ARYLOXY-4-PHENYL-AZET-2-ONE

This is a continuation of application Ser. No. 120,428, filed Feb. 11, 1980, abandoned.

BACKGROUND OF THE INVENTION

A process for condensing aldehydes with amines is disclosed in *J. Organic Chemistry*, vol. 41, pp. 3491-3 (1976).

N-Acyl-3-aryl-3-azetidinol intermediates are disclosed in U.S. Pat. No. 4,088,644.

DESCRIPTION OF THE INVENTION

The plant-growth-regulating compound of my invention may be represented by the following formula (I):

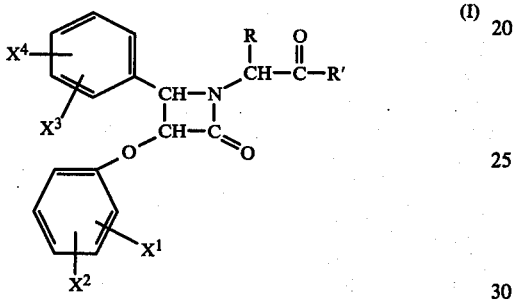

wherein R is hydrogen or alkyl of 1 to 3 carbon atoms; R' is hydrogen, alkyl of 1 to 6 carbon atoms, alkoxy of 1 to 6 carbon atoms, alkylthio of 1 to 6 carbon atoms, or $NR^1R^2$ wherein $R^1$ and $R^2$ are independently hydrogen or alkyl of 1 to 12 carbon atoms; and $X^1$, $X^2$, $X^3$ and $X^4$ are independently hydrogen, chloro, bromo, fluoro, iodo, alkyl of 1 to 4 carbon atoms or alkoxy of 1 to 4 carbon atoms.

Representative R' groups are methyl, ethyl, i-propyl, n-propyl, n-butyl, sec-butyl, n-pentyl, isohexyl, methoxy, ethoxy, n-propoxy, i-propoxy, methylthio, ethylthio, hexylthio, amino, methylamino, dimethylamino, methylethylamino, decylamino, dodecylamino.

Preferably R' is alkoxy of 1 to 6 carbon atoms. Most preferably R' is ethoxy.

Representative $X^1$, $X^2$, $X^3$ and $X^4$ groups are chloro, bromo, fluoro, iodo, methyl, ethyl, i-propyl, n-butyl, methoxy, i-propoxy, sec-butoxy.

Preferably $X^1$, $X^2$, $X^3$, $X^4$ and R are hydrogen.

The compounds of my invention may be prepared according to the following scheme:

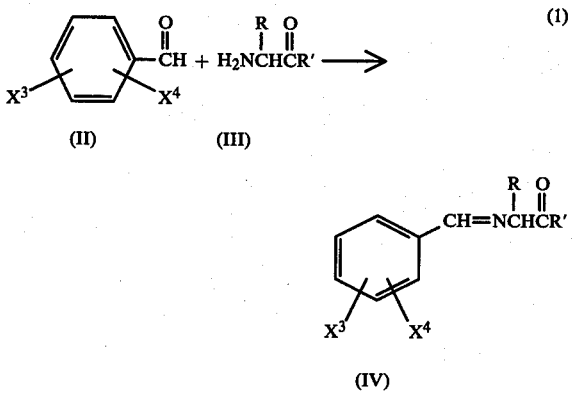

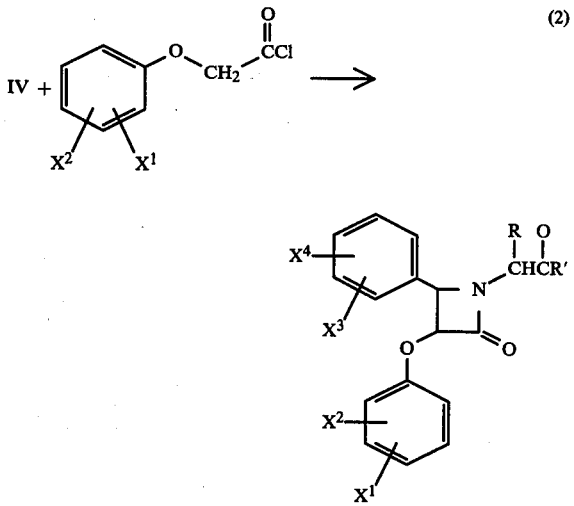

Reaction (1) may be conducted in a suitable organic diluent at ambient temperature and atmospheric pressure. Preferably the hydrochloride salt of the amine (III) may be used and the reaction may then be conducted in presence of a base, such as trialkylamine, to scavenge the hydrogen chloride. The reaction may be conducted in the presence of a dehydrating agent, such as magnesium sulfate, to scavenge the water by-product.

Reaction (2) may be conducted in a suitable organic diluent at ambient temperature at atmospheric pressure. The reaction is preferably conducted in the presence of a base, such as trialkylamine, to scavenge evolved hydrogen chloride.

EXAMPLE 1

Preparation of Benzaldehyde Carbethoxymethylimine

To ethyl glycinate hydrochloride (36.4 g) suspended in 500 ml methylene chloride were added magnesium sulfate (22 g) and triethylamine (72 ml, 52.4 g). Benzaldehyde (27.6 g) was added dropwise at 15°-20° C. with stirring. The mixture was stirred at room temperature for two hours, filtered and stripped. To the residue was added 300 ml diethylether and 150 ml brine. After separation the organic layer was collected, and the aqueous layer was extracted with 100 ml ether. The organic phases were combined, dried (MgSO$_4$), filtered and stripped to yield the title product as a pale yellow oil.

EXAMPLE 2

Preparation of 1-Carbethoxymethyl-3-phenoxy-4-phenyl-azet-2-one

To a solution of phenoxyacetyl chloride (10.8 g) in 30 ml benzene was added dropwise a solution of the imine product (12 g) prepared in Example 1 in 50 ml benzene. The reaction was exothermic. The mixture was stirred at room temperature for 20 minutes, then 7.5 g triethylamine was added dropwise. The mixture was refluxed for 90 minutes and allowed to stand overnight at room temperature.

The mixture was poured into 200 ml ice water and 150 ml methylene chloride and the layers were separated. The organic layer was washed with water, dried (MgSO$_4$), filtered and stripped to yield a yellow oil. The oil was chromatographed on silica gel (eluted with 50:50 methylene chloride:benzene) to yield the title product as a yellow oil. The testing of this product is reported in Table I as Compound 1. Calc. C:70.1, H:5.9; N:4.3; Fd. C:68.46, H:5.86, N:3.97.

Following procedure analogous to Examples 1 and 2, the compound 1-carbethoxymethyl-3-2,4-dichlorophenoxy-4-phenylazet-2-one was prepared. The results of testing are shown in Table II as Compound 2. Calc. C:57.9, H:4.3, N:3.6; Fd. C:57.88, H:4.55, N:3.48.

UTILITY

The compounds of the present invention are, in general, herbicidal and plant-growth regulating in post-emergent applications. The compounds are particularly effective as post-emergent plant-growth-regulators.

The compounds, when applied to the soil surrounding growing plants in such an amount that the compounds will not kill beneficial plants, also show efficient plant growth regulating or retarding effects and may be advantageously employed, for example, to prevent or retard the growth of lateral buds in plants and to promote the thinning out of superfluous fruits in various fruit trees.

The compounds can be applied in any of a variety of compositions. In general, the compounds can be extended with a carrier material of the kind used and commonly referred to in the art such as inert solids, water and organic liquids.

The compounds will be included in such compositions in sufficient amount so that they can exert a growth-regulating effect. Usually from about 0.5 to 95% by weight of the compounds are included in such formulations.

Solid compositions can be made with inert powders. The compositions thus can be homogeneous powders that can be used as such, diluted with inert solids to form dusts, or suspended in a suitable liquid medium for spray application. The powders usually comprise the active ingredient admixed with minor amounts of conditioning agent. Natural clays, either absorptive, such as attapulgite, or relatively non-absorptive, such as china clays, diatomaceous earth, synthetic fine silica, calcium silicate and other inert solid carriers of the kind conventionally employed in powdered growth-regulating compositions can be used. The active ingredient usually makes up from 0.5-90% of these powder compositions. The solids ordinarily should be very finely divided. For conversion of the powders to dusts, talc, pyrophyllite, and the like, are customarily used.

Liquid compositions including the active compounds described above can be prepared by admixing the compound with a suitable liquid diluent medium. Typical of the liquid media commonly employed are methanol, benzene, toluene, and the like. The active ingredient usually makes up from about 0.5 to 50% of these liquid compositions. Some of these compositions are designated to be used as such, and others to be extended with large quantities of water.

Compositions in the form of wettable powders or liquids can also include one or more surface-active agents, such as wetting, dispersing or emulsifying agents. The surface-active agents cause the compositions of wettable powders or liquids to disperse or emulsify easily in water to give aqueous sprays.

The surface-active agents employed can be of the anionic, cationic or nonionic type. They include, for example, sodium long-chain carboxylates, alkyl aryl sulfonates, sodium lauryl sulfate, polyethylene oxides, lignin sulfonates and other surface-active agents.

The amount of compound or composition administered will vary with the particular plant part or plant growth medium which is to be contacted, the general location of application—i.e., sheltered areas such as greenhouses, as compared to exposed areas such as fields—as well as the desired type of control. For plant growth regulating or retarding activity, it is essential to apply the compounds at a concentration not so high as to kill the plants. Therefore, the application rates for plant growth regulating or retarding activity will generally vary from 0.1 to 5 kg/ha, and preferably from 0.1 to 3 kg/ha.

Plant-growth-regulating tests on representative compounds of the invention were made using the following methods.

PLANT-GROWTH-REGULATING TEST

Uniform size Idaho 1-11 pinto beans, 13-16 days old, 1 plant per 4" pot, were used with monofoliate leaves fully developed and first trifoliates beginning to unfold. Sufficient plants for 4 replicates per treatment were selected. On each plant all growth 5 mm above the monofoliate leaf node was removed with forceps one to four hours before application.

As a stock solution 100 mg of test material was dissolved in 10 ml of acetone. Aliquots of 150 ml were prepared of 200, 80 and 32 ppm by bringing 3, 1.2 and 0.48 ml to the 150 ml volume with 147, 148.8 and 149.52 ml deionized water respectively. This is equivalent to 75, 30 and 12 gamma/$cm^2$ of soil area for the three rates.

To each of 4 pots, each containing one Pinto bean plant, 30 ml of test solution was applied to the soil surface using the 30 ml syringe or other suitable metering device. The plants were incubated in a greenhouse maintained at 70°-80° F. The plants were kept off the bottom of the metal greenhouse trays by using expanded metal supported an inch above the tray. The plants were watered by overhead irrigation throughout the course of the test.

Plants were evaluated 12 to 16 days after treatment. The following signs of physiological activity were noted: flowering, bud break at the cotyledonary node, side branching, compactness of the plant (a measure of internodal length), phytotoxicity/dessication/defoliation and relative green color (a measure of leaf thickness). These qualities were compared to plants treated by the standard, tri-iodo benzoic acid (TIBA), and to untreated check plants (denoted as "Check (−)" in Table I). Untreated check plants denoted as (+) were those on which the monofoliate leaf nodes were not removed. The results are shown in Table I.

TABLE I

| | | Plant Growth Regulation Of Pinto Bean Plants | | | | | | |
|---|---|---|---|---|---|---|---|---|
| Compound | Conc. $\gamma/cm^2$ | Flowering | Bud Break Cotyl.Node | Side Branching | Compactness | Phyto/ Dess/ Def | Green Color | Other Notes |
| 1 | 75.0 | B,C | 10 | 10 | 0 | 1 | 9 | 1 |
| | 30.0 | B,C | 9 | 9 | 1 | 4 | 6 | 1 |
| | 12.0 | C | 5 | 7 | 3 | 4 | 5 | — |

TABLE I-continued

Plant Growth Regulation Of Pinto Bean Plants

| Compound | Conc. γ/cm² | Flowering | Bud Break Cotyl.Node | Side Branching | Compactness | Phyto/ Dess/ Def | Green Color | Other Notes |
|---|---|---|---|---|---|---|---|---|
| TIBA | 75.0 | B | 8 | 8 | 9 | 7 | 4 | D |
|  | 30.0 | A,B | 8 | 9 | 8 | 5 | 5 | — |
|  | 12.0 | A,B | 8 | 7 | 6 | 6 | 4 | — |
| Check − | — | A | 5 | 5 | 5 | 5 | 5 | — |
| Check + | — | A | 3 | 3 | 3 | 5 | 5 | — |

A Normal, same as check
B Delayed flowering
C Heavy flower abortion
D Tight cluster of growth
E No growth from ax. bud
F Very little growth
G Pt desiccation along vein
H Roots coming out from soil
I Dead plant
Effectiveness - 0 = none
5 = normal
10 = high

ROOT INHIBITION OF SEEDLINGS

Ten seeds each of watergrass, mung beans and cucumbers were placed in each of several Northrup-King Seed-Pack growth pouches. To each pouch was added 15 ml of an aqueous solution at the test concentration of compound 2. The pouches were suspended in containers under 125–150 footcandles of light for six days at room temperature. Root length is measured for each species and expressed as percent inhibition compared to untreated check samples. Activity is compared with the standard MH-30 (maleic hydrazide).

The results are shown in Table II.

TABLE II

ROOT INHIBITION (% Inhibition)

| | Concentration, ppm | | | |
|---|---|---|---|---|
| | 313 | 125 | 50 | 20 |
| WATERGRASS | | | | |
| Compound 2 | 0 | 0 | 4 | 0 |
| Standard | 84 | 76 | 68 | 55 |
| MUNG BEANS | | | | |
| Compound 2 | 0 | 0 | 0 | 0 |
| Standard | 86 | 84 | 81 | 61 |
| CUCUMBERS | | | | |
| Compound 2 | 59 | 39 | 51 | 5 |
| Standard | 77 | 62 | 65 | 45 |

What is claimed is:

1. A compound of the formula

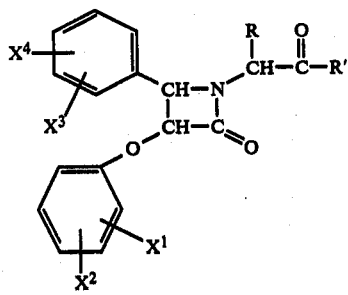

(I)

wherein R is hydrogen or alkyl of 1 to 3 carbon atoms; $R'$ is hydrogen, alkyl of 1 to 6 carbon atoms, alkoxy of 1 to 6 carbon atoms, alkylthio of 1 to 6 carbon atoms, or $NR^1R^2$ wherein $R^1$ and $R^2$ are independently hydrogen or alkyl of 1 to 12 carbon atoms; and $X^1$, $X^2$, $X^3$ and $X^4$ are independently hydrogen, chloro, bromo, fluoro, iodo, alkyl of 1 to 4 carbon atoms or alkoxy of 1 to 4 carbon atoms.

2. A compound according to claim 1 wherein $R'$ is alkoxy of 1 to 6 carbon atoms.

3. A compound according to claim 2 wherein R is hydrogen.

4. A compound according to claim 3 wherein $X^1$, $X^2$, $X^3$ and $X^4$ are independently hydrogen, chloro, bromo, fluoro or iodo.

5. The compound according to claim 4 wherein $X^1$, $X^2$, $X^3$ and $X^4$ are hydrogen $R'$ is ethoxy.

6. The compound of the formula:

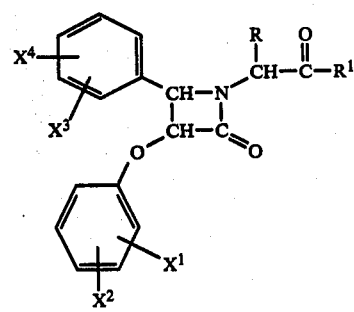

wherein R is hydrogen, $X^1$ and $X^2$ are 2-chloro and 4-chloro, respectively, $R^1$ is ethoxy, and $X^3$ and $X^4$ are hydrogen.

7. A plant-growth-regulating composition comprising a biologically inert carrier and a plant-growth-regulating effective amount of a compound of the formula defined in claim 1.

8. The composition of claim 7 wherein $R'$ is ethoxy, and R, $X^1$, $X^2$, $X^3$ and $X^4$ are hydrogen.

9. A method for regulating the growth of vegetation comprising applying to said vegetation or its habitat a growth regulating effective amount of a compound of the formula defined in claim 1.

10. The method of claim 9 wherein $R'$ is ethoxy and R, $X^1$, $X^2$, $X^3$ and $X^4$ are hydrogen.

* * * * *